United States Patent [19]

Cordell et al.

[11] Patent Number: 5,221,607
[45] Date of Patent: Jun. 22, 1993

[54] ASSAYS AND REAGENTS FOR AMYLOID DEPOSITION

[75] Inventors: Barbara Cordell; David Wolf, both of Palo Alto, Calif.

[73] Assignee: Scios Nova Inc., Mountain View, Calif.

[21] Appl. No.: 785,142

[22] Filed: Oct. 29, 1991

Related U.S. Application Data

[63] Continuation of Ser. No. 408,767, Sep. 18, 1989, abandoned.

[51] Int. Cl.$^5$ .................... C12Q 1/68; C07K 13/00; C12N 15/00
[52] U.S. Cl. ........................... 435/6; 435/7.21; 435/70.1; 435/70.3; 435/172.1; 435/240.1; 435/240.2; 435/320.1; 436/811; 536/23.5; 530/330; 530/350; 530/806; 530/839
[58] Field of Search .............. 435/6, 70.1, 172.3, 435/810, 7.21, 70.3, 172.1, 240.1, 240.2, 320.1; 436/543, 548, 808, 811; 530/300, 350, 387, 806, 808, 810, 839; 536/27

[56] References Cited

U.S. PATENT DOCUMENTS

| | | | |
|---|---|---|---|
| 4,264,729 | 4/1981 | Beljanski | 435/6 |
| 4,603,112 | 7/1986 | Paoletti et al. | 435/235 |
| 4,666,829 | 5/1987 | Glenner et al. | 435/6 |
| 4,912,206 | 3/1990 | Goldgaber et al. | 536/27 |
| 4,919,915 | 4/1990 | Averback | 424/7.1 |

FOREIGN PATENT DOCUMENTS

| | | |
|---|---|---|
| 0304013 | 2/1989 | European Pat. Off. . |
| 8906689 | 7/1989 | PCT Int'l Appl. . |
| 8906693 | 7/1989 | PCT Int'l Appl. . |
| WO89/07657 | 8/1989 | PCT Int'l Appl. . |

OTHER PUBLICATIONS

Kohler et al., "Continuous Cultures of Fused Cells Secreting Antibody of Defined Specificity", *Nature*, vol. 256, pp. 495–497 (1975).

Robakis et al., "Molecular Cloning and Characterization of a CDNA Encoding the Cerebrovascular and the Neuritic Plaque Amyloid Peptides", *Proc. Natl. Acad. Sci. USA*, vol. 84, pp. 4190–4194 (1987).

Selkoe et al., "B-Amyloid Precursor Protein of Alzheimer Disease Occurs as 110– to 135-Kilodalton Membrane-Associated Proteins in Neural and Nonneural Tissues", *Proc. Natl. Acad. Sci. USA*, vol. 85, pp. 7341–7345 (1988).

Wong et al., (1985) *Proc Natl Acad Sci* 82:8729–8732.
Kang et al., (1987) *Nature* 325:733–736.
Ponte et al., (1988) *Nature* 331:525–527.
Tanzi et al., (1988) *Nature* 331:528–530.
Kitaguchi et al., (1988) *Nature* 331:530–532.
Castano and Frangione, (1988) *Lab Invest* 58:122–132.
Roth et al., (1966) *Nature* 209:109–110.
Wilcock and Esiri (1982) *J Neurol Sci* 56:343–356.
Coria et al., (1988) *Lab Invest* 58:454–458.
Ravid et al., (1977) *Ann Intern Med* 87:568–570.
Castano et al., (1986) *Biochem Biophys Res Comm* 141:782–789.
Kirschner et al., (1987) *Proc Natl Acad Sci USA* 84:6953–6957.
Dyrks et al., (1988) *EMBO J* 7:949–957.

*Primary Examiner*—Robert A. Wax
*Assistant Examiner*—Richard C. Ekstrom
*Attorney, Agent, or Firm*—Morrison & Foerster

[57] ABSTRACT

The present invention provides an in vitro tissue culture-based assay for amyloid deposition specific for Alzheimer's disease which is suitable for routine drug screening analysis. Immunological diagnostic reagents for Alzheimer's disease are also provided.

7 Claims, 4 Drawing Sheets

ASSAYS AND REAGENTS FOR AMYLOID DEPOSITION

This application is a continuation of application Ser. No. 07/408,767, filed Sep. 18, 1989, now abandoned.

FIELD OF THE INVENTION

The present invention relates to assays and reagents useful for the chemical intervention of amyloidosis in Alzheimer's disease.

BACKGROUND OF THE INVENTION

Alzheimer's disease (AD) is an age-related brain degenerative disease that is the most common cause of intellectual failure in late life. Neuritic or senile plaques and neurofibrillary tangles (NFT) are the hallmark characteristic of the histopathology of Alzheimer's brains. These plaques and tangles are believed to result from deposits of two different proteins which share the properties of the amyloid class of proteins specific for AD.

The major protein component of amyloid is an ~4 kilodalton (kd) protein, designated the beta-protein or A4 protein due to a partial beta pleated structure or its molecular weight, respectively. The amino acid sequence of A4 has been defined (Wong et al., (1985) *Proc Natl Acad Sci USA* 82:8729-8732) and full-length cDNA encoding a primary translation product of 695 residues has been cloned (Kang et al., (1987) *Nature* 325:733-736) while other cDNAs have been identified which encode a 751-residue or 770-residue precursor form (Ponte et al., (1988) *Nature* 331:525-527; Tanzi et al., (1988) *Nature* 331:528-530; and Kitaguchi et al., (1988) *Nature* 331:530-532).

The A4 protein accumulates extracellularly, both in brain parenchyma and in the walls of blood vessels, generally as amyloid plaques which form aggregate fibril structures and are insoluble on SDS-polyacrylamide gels. The fibrils are generally identified as amyloid based on their green birefringence after staining with Congo red and their 40- to 90-A diameter.

The second protein, mentioned previously, accumulates intracellularly in neurons of Alzheimer's brains (Castano and Frangione, (1988) *Lab Invest* 58:122-132) and forms tangles composed of structures resembling paired helical filaments (PHFs). In contrast to the beta-amyloid protein, the primary structure and number of proteins comprising PHFs are unknown. PHF-containing neurites are found in the periphery of the plague, whereas deposits of beta-amyloid protein form the central core of mature plaques, surrounded by degenerated neurites and glial cells.

Although the etiology of AD is unknown, it has been demonstrated that the frequency of neuritic plaques found in the cortex of AD patients correlates with the degree of dementia (Roth et alo., (1966) *Nature* 209:109-110; Wilcock ad Esiri, (1982) *J Neurol Sci* 56:343-356). The therapeutic goals in amyloidosis are to prevent further deposition of amyloid material and to promote or accelerate its resorption. To date, there are no means available to treat the pathogenesis of AD and the paucity of understanding concerning the mechanism of amyloid formation in AD is a major obstacle in the development and design of therapeutic agents that can intervene in this process. Moreover, no animal models for brain amyloidosis with beta-amyloid protein deposits or PHFs exist, creating yet another obstacle to test such putative therapeutic agents.

Logical therapeutic approaches are now, however, emerging for treating the particular amyloidosis associated with AD. These approaches are attributable, in part, from the successes and failure gained in attempting to treat other forms of amyloidosis, such as the use of dimethyl sulfoxide which blocks amyloid formation from Bence Jones proteins in vitro (Coria et al., (1988) *Lab Invest* 58:454-458) and use of colchicine to reduce the size of renal amyloid deposits and induce clinical remissions in several cases of familial Mediterranean fever and amyloid nephropathy (Ravid et al., (1977) *Ann Intern Med* 87:568-570).

Efforts directed to the design of in vitro models of age-related cerebral amyloidogenesis using A4-derived synthetic peptides are disclosed in Castano et al., (1986) *Biochem Biophys Res Comm* 141:782-789, and in Kirschner et al., (1987) *Proc Natl Acad Sci USA* 84:6953-6957. Castano et al. demonstrated that amyloid fibrils could be formed in vitro when using a synthetic peptide corresponding to the amino-terminal 28 residues of the amyloid core protein. This 28 residue peptide, as well as a 17 residue sequence contained within the 28 amino acids, both formed fibrils which stain similarly to material a 17 residue seqeunce contained within the 28 amino acids, amyloid fibrils were soluble, unlike the naturally occurring insoluble amyloid isolated from Alzheimer's brains. Kirschner et al. demonstrated that the same 28 residue peptide could be produced as an insoluble aggregate; however, this particular in vitro model is not expected to correlate well to the cellular environment in which amyloid deposition occurs.

Dyrks et al., (1988) *EMBO J* 7:949-957 showed that a shortened cell-free translation product comprising the amyloid A42 part and the cytoplasmic domain of the 695-residue precursor can form multimers. While aggregation was observed employing an in vitro cell-free system, this system fails to reveal whether aggregation of the translation product would naturally follow in vivo. Moreover, the in vitro cell-free system does not address protein stability issues, that is, whether adequate levels of the protein could be expressed, whether protein proteolysis exists, and other concerns generally associated with in vivo expression of recombinant proteins.

Therefore, there exists a need for a definitive cellular deposition model with which one may assay agents capable of chemically intervening in the process of amyloid deposition. Such a method should be relatively simple to perform and should be highly specific in distinguishing AD plaques from the plaques associated with other disorders. Furthermore, it is desirable that the assay be capable of being reduced to a standardized format. The present invention satisfies such needs and provides further advantages.

SUMMARY OF THE INVENTION

The present invention provides a method for determining the ability of a potential therapeutic agent to intervene in the amyloid deposition process associated with Alzheimer's disease in a cellular environment, which method utilizes a recombinantly produced amyloid substrate in a screening assay. The present invention also allows for the development and use of immunological reagents to detect the formation of preamyloid protein aggregation in the cell lines provided by the invention.

To achieve the objects and in accordance with the purpose of the invention, as embodied and broadly described herein, a method of screening agents capable of intervention in Alzheimer's disease amyloidosis comprises:

a) culturing a cell line capable of expressing a gene encoding beta-amyloid protein under conditions suitable to produce the beta-amyloid protein as an insoluble, preamyloid aggregate;

b) combining a known quantity of the agent to be tested to the cell culture; and c) monitoring the combination to determine whether the preamyloid aggregate formation is reduced.

In an alternative embodiment of the invention, preamyloid formation can be induced through infection of a cell line with a recombinant virus capable of expressing the beta-amyloid protein as an insoluble preamyloid aggregate. Such recombinant viruses carry expression vectors comprising DNA encoding the beta-amyloid protein.

Immunoassay kits employing the reagents useful to screen potential amyloid intervening agents are also provided by the present invention.

BRIEF DESCRIPTION OF THE DRAWINGS

FIG. 3A is a Mock control; FIG. 3B is a VV:CONT control; FIG. 3C is the VV:99 construct; and FIG. 3D is the VV:42 construct. The magnification is 200x with a 0.4 second exposure time for each photo.

DETAILED DESCRIPTION OF THE PREFERRED EMBODIMENTS

Figure 1:
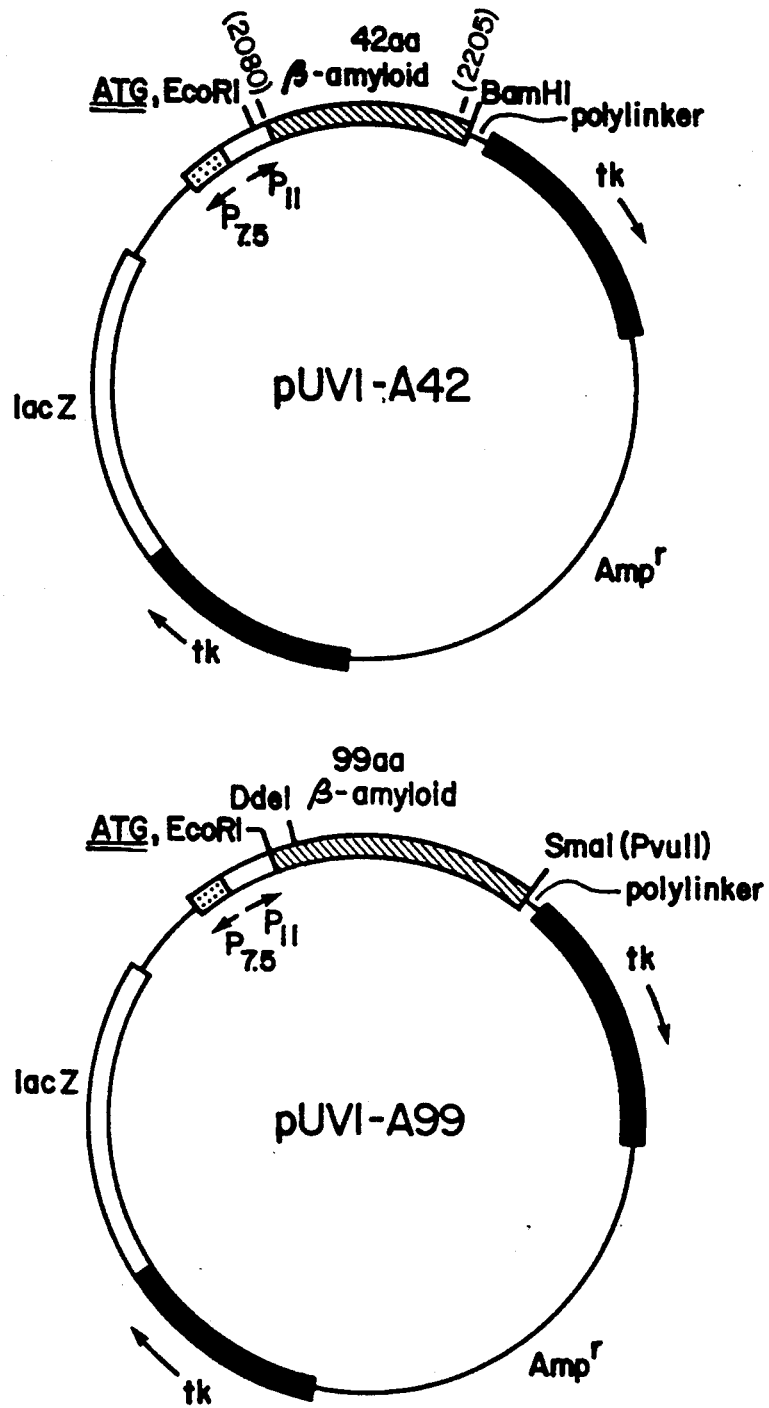
FIG. 1 is a schematic illustration of two amyloid expression constructs employing the vaccinia pUV1 insertion vector.

As indicated above, the invention involves a method of screening agents capable of intervention in Alzheimer's disease amyloidosis.

As used herein, the term "beta-amyloid core protein" or "A4 protein" refers to an approximately 4 kd protein first identified by Glenner and Wong, (1984) *Biochem Biophys Res Comm* 120:885, which is defined at the amino terminus by sequence analysis as a mixture of four peptides with slightly different amino termini, the amino termini of the three smaller peptides being completely encoded by that of the largest.

The term "beta-amyloid precursor protein" refers to either the amyloid precursor protein of 695 amino acids (Kang et al., (1987) supra) or the 751 amino acid protein (Ponte et al., (1988) supra) containing within their sequence, the beta-amyloid core protein sequence defined above. The A4 core protein begins at amino acid 597 of the 695 amino acid protein and at amino acid 653 of the 751 amino acid sequence.

The terms "preamyloid aggregation", "preamyloid formation", or "preamyloid deposits" refer to a morphological description—first discovered by Tagliavini et al., (1988) *Neurosci Lett* 93:191-196—of spherical, granular deposits which are considerably smaller than pre-plaques and plaques found at a high frequency in the brains of Alzheimer's victims. These deposits can be occasionally detected with silver stain but not with Congo red, a stain to which amyloid proteins demonstrate high binding affinity.

As used herein, the term "insertion vector" includes plasmids, cosmids or phages capable of mediating homologous recombination into a viral genome such that the DNA encoding the beta-amyloid protein is stably carried by the resulting recombinant virus. In one embodiment of the invention plasmids constructed from vaccinia virus DNA are employed.

The term "expression vector" includes plasmids, cosmids or phages capable of synthesizing a protein encoded by the respective recombinant gene carried by said vector. Such vectors are independently replicated in or capable of integration into the chromosome of an appropriate host cell for expression of the amyloid protein.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells, for example, the transforming DNA may be maintained on an episomal element such as a plasmid. The cell has been stably transformed when the cell is able to establish cell lines or clones comprised of a population of daughter cells containing the transforming DNA. A "clone" is a population of cells derived from a single cell or common ancestor by mitosis. A "cell line" is a clone of a cell that is capable of stable growth in vitro for many generations.

A. Beta-Amyloid Coding Sequences

The beta-amyloid genes may be synthetic or natural, or combinations thereof. The gene encoding the natural 751 amino acid precursor protein is described in PCT WO88/03951, published Jun. 2, 1988 and assigned to the same assignee of the present application, and the expression of the protein in mammalian cells is provided in Example 4 therein. The relevant portions of this publication are specifically incorporated herein by reference.

The genes encode the A42 core protein or an amyloid protein, A99, which comprises the A42 core protein and the cytoplasmic domain. This latter protein consists of the 42 residue core protein and 57 amino acids of the cytoplasmic domain of the 751 precursor protein. The sequence of A99 is as follows:

```
                         10
Asp Ala Glu Phe Arg His Asp Ser Gly Tyr Glu Val His His Gln 20                                  30
Lys Leu Val Phe Phe Ala Glu Asp Val Gly Ser Asn Lys Gly Ala 40    (42)
Ile Ile Gly Leu Met Val Gly Gly Val Val Ile Ala Thr Val Ile 50                                  60
Val Ile Thr Leu Val Met Leu Lys Lys Lys Gln Tyr Thr Ser Ile

70
His His Gly Val Val Glu Val Asp Ala Ala Val Thr Pro Glu Glu 80                                  90
Arg His Leu Ser Lys Met Gln Gln Asn Gly Tyr Glu Asn Pro Thr
```

-continued
(99)
Tyr Lys Phe Phe Glu Gln Met Gln Asn.

These genes are provided for expression of the desired protein using recombinant DNA expression vectors.

As mentioned above, these genes may be natural, synthetic or combinations thereof. When preparing a synthetic nucleotide sequence, it may be desirable to modify the natural amyloid nucleic acid sequence. For example, it will often be preferred to use codons which are preferentially recognized by the desired host. In some instances, it may be desirable to further alter the nucleotide sequence, either synthetic or natural, to create or remove restriction sites to, for example, enhance insertion of the gene sequence into convenient expression vectors or to substitute one or more amino acids in the resulting polypeptide to increase stability. A general method for site-specific mutagenesis is described in Noren et al., (1989) *Science* 244:182–188.

Peptides of this precursor protein, for example, those derived from the A4 core protein, are also provided herein for the generation of specific immunological reagents and may also be synthetic or natural. Synthetic oligonucleotides are prepared by either the phosphotriester method as described by Edge et al., (1981) *Nature* 292:756 and Duckworth et al., (1981) *Nuc Acids Res* 9:1691 or the phosphroamidite method as described by Beaucage and Caruthers, (1981) *Tet Lett* 22:1859 and Matteucci and Caruthers, (1981) *J Am Chem Soc* 103:3185, and can be prepared using commercially available automated oligonucleotide synthesizers.

B. Vaccinia Viral Vectors

The coding sequences for the amyloid proteins can be inserted into vaccinia virus plasmid insertion vectors for the purpose of generating recombinant vaccinia viruses using the methods described in Moss et al., (1983) *Methods in Gene Amplification*, Vol. 3, Elsevier-North Holland, p. 202–213; and in Moss et al., (1984) *J Virol* 49:857:864. The amyloid-vaccinia recombinants can then be used for (1) expression of the respective amyloid protein and analysis for preamyloid formation, and (2) production of amyloid antibodies.

The two vaccinia virus insertion vectors, pSC11 (Chakrabarti et al., (1985) *Mol Cell Biol* 5:3403–3409 and pUV1 (Falkner et al., (1987) *Nuc Acids Res* 15:7192) were used for the expression of the amyloid proteins and generation of amyloid-vaccinia recombinants. Both vectors are of the co-insertion variety and each contains two vaccinia virus promoters. One promoter (P1) is used to drive the expression of a selectable marker gene (in this case, beta-galactosidase) while the other promoter (P2) is used to drive expression of the heterologous amyloid DNA insert. Both are flanked by vaccinia virus DNA (an interrupted thymidine kinase [tk] gene) which facilitates homologous recombination into a wild-type vaccinia virus genome and provides a selection mechanism (generation of tk minus viruses). The pSC11 vector utilizes a vaccinia early-late promoter (P7.5) to drive heterologous gene expression and has a single SmaI cloning site. The pUV1 vector utilizes a vaccinia late promoter (P11) to drive heterologous gene expression and is designed for the expression of fusion proteins behind the ATG of the P11 late gene. In all cases, amyloid-pUV1 constructs were made using the most 5' (after the ATG) cloning site (EcoRI) in order to avoid introduction of additional amino terminal amino acids into the native amyloid protein sequence.

C. Recombinant Expression Vectors and Hosts

It will also be understood by those skilled in the art that both procaryotic and eucaryotic systems may be used to express the amyloid genes described herein. Procaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar et al., (1977) *Gene* 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillianse) and lactose (lac) promoter systems (Chang et al., (1977) *Nature* 198:1056), the tryptophan (trp) promoter system (Goeddel et al., (1980) *Nucleic Acids Res* 8:4057), the lambda-derived $P_L$ promoter (Shimatake et al., (1981) *Nature* 292:128) and N-gene ribosome binding site, and the trp-lac (trc) promoter system (Amann and Brosius, (1985) *Gene* 40:183).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2 micron origin of replication of Broach, (1983) *Meth Enz* 101:307, or other yeast compatible origins of replication (see, for example, Stinchomb et al., (1979) *Nature* 282:39; Tschumper et al., (1980) *Gene* 10:157 and Clarke et al., (1983) *Meth Enz* 101:300) may be used. Control sequences for yeast vectors include promoters for the synthesis of glycolytic enzymes (Hess et al., (1968) *J Adv Enzyme Reg* 7:149; Holland et al., (1978) *Biochemistry* 17:4900). Additional promoters known in the art include the promoter for 3-phosphoglycerate kinase (Hitzeman et al., (1980) *Biol Chem* 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polyppetides in eucaryotic host cell cultures derived from multicellular organisms. See, for example, Axel et al., U.S. Pat. No. 4,399,216. These systems have the additional advantage of the ability to splice out introns and thus can be used directly to express genomic fragments. Useful host cell lines include VERO, HeLa, baby hamster kidney (BHK), CV-1, COS, MDCK, NIH 3T3, L, and Chinese hamster ovary (CHO) cells. Expression vectors for such cells ordinarily include promoters and control sequences compatible with mammalian cells such as, for example, the commonly used early and late promoters from Simian Virus 40 (SV40) (Fiers et al., (1978) *Nature* 273:113), or other viral promoters such as those derived from polyoma, herpes virus, Adenovirus 2, bovine papilloma virus, or avian sarcoma viruses. The controllable promoter, hMTII (Karin et al., (1987) *Nature* 299:797–802) may also be used. General aspects of mammalian cell host system transformations have been described by Axel, supra.

Insect expression systems may also be employed to express the amyloid genes. For example, the baculovirus polyhedrin gene has been employed for high-level expression of heterologous proteins (Smith et al., (1983) *Mol Cell Biol* 3(12):2156–2165; Summers et al., "Genetic Engineering of the Genome of the *Autographa Californica* Nuclear Polyhedrosis Virus", Banbury Report: Genetically Altered Viruses in the Environment, 22:319–339, Cold Spring Harbor Laboratory, 1985).

D. Generation of Stably Transfected Cell Lines

The amyloid DNA clones expressed in vaccinia can also be used to generate stably transfected cell lines expressing the amyloid proteins. In general, these cell lines are generated by first constructing one of two expression plasmids. In both expression plasmids, the selectable marker is provided by a G418 neomycin expression cassette (neo) consisting of the SV40 early promoter, the bacterial kanamycin-resistance gene also containing its own promoter, the SV40 intervening sequence, and the SV40 polyadenylation site from the early region. In the first expression plasmid, the amyloid DNA cloning site is flanked at the 5' end by the human metallothionein gene promoter, pMtIIa, modified with an SV40 enhancer, and at the 3' end by the SV40 polyadenylation site from the early region. In the second expression construct, the amyloid DNA cloning site is flanked at the 5' end by a beta-actin promoter, and at the 3' end by a sequence encoding a useful polyadenylation site, such as that of the SV40 early region or the beta-actin gene.

Each of the vectors described above can be transformed into a mammalian cell line such as, but not limited to, those described in the following examples by either calcium phosphate-DNA coprecipitation or electroporation. A day later, the cells are subjected to 1 mg/ml G418 to provide pools of G418-resistant colonies. Successful transformants, also having a stable inheritance of the DNA contained in the expression construct, are then plated at low density for purification of clonal isolates. Clonal isolates are then analyzed for maximum production of the amyloid protein of interest and high-producing clones are expanded to serve as stock.

E. Detection Methods for Preamyloid Formation

The diagnosis of amyloidosis is established by demonstration of the characteristic emerald-green birefringence of tissue specimens stained with Congo red and examined by polarization microscopy. Congo red staining is generally carried out using commercially available diagnostic kits. The isolation and characterization of the A4 protein has allowed specific antibodies to be raised that recognized cerebral amyloid in Alzheimer's disease (Allsop et al( 1986) *Neurosci Lett* 68:252-256). Moreover, Tagliavini et al., (1988) supra, have demonstrated that antibodies can be generated which detect in both Alzheimer's patients and to a lesser extent in nondemented individual's preamyloid deposits, which deposits lack the tinctorial and optical properties of amyloid and are, therefore, undetectable using conventional staining methods employing principally Congo red, but also thioflavin S or silver salts.

Standard protocols can be employed for preparing antibodies directed against the amyloid proteins of the invention. Techniques for preparing both polyclonal and monoclonal antibodies are well known in the art. Briefly, polyclonal antibodies are prepared by injecting amyloid protein or synthetic amyloid peptides with an adjuvant into an animal such as rabbits or mice. The amyloid protein may need to be conjugated to a carrier protein such as bovine serum albumin or keyhole limpet hemacyanin using a chemical process which employs carbodiimide, glutaraldehyde, or other cross-linking agents. Alternatively, the protein may be administered without being conjugated to a carrier protein. Vaccinia virus recombinants which are expressing amyloid proteins may also be used to prepare antibodies. The vaccinia virus recombinants are injected into an animal and then the animal is boosted several weeks after the initial immunization. Ten days to two weeks later the animals are bled and antiserum is collected and analyzed for titer.

Monoclonal antibodies are commonly prepared by fusing, under appropriate conditions, B-lymphocytes of an animal which is making polyclonal antibodies with an immortalizing myeloma cell line. The B-lymphocytes can be spleen cells or peripheral blood lymphocytes. Techniques for fusion are also well known in the art, and in general, involve mixing the cells with a fusing agent such as polyethylene glycol. Successful hybridoma formation is assessed and selected by standard procedures such as, for example, HAT medium. From among successful hybridomas, those secreting the desired antibody are screened by assaying the culture medium for their presence.

Standard immunological techniques such as ELISA (enzyme-linked immunoassay), RIA (radioimmunoassay), IFA (immunofluorescence assay) and Western blot analysis, which are well known in the art, can be employed for diagnostic screening for amyloid expression. A vast literature now exists with respect to various modifications of the basic assay principle, which is simply that there must be a specific association between target analyte and antibody, which association is detectable qualitatively and/or quantitatively. Fluorescent, enzymatic, or radioactive labels are generally used.

One typical arrangement utilizes competition, between labeled antigen (e.g. amyloid protein) and the analyte, for the antibody, followed by physical separation of bound and unbound fractions. Analyte competes for the binding of the labeled antigen; hence more label will remain in the unbound fraction when larger amounts of analyte are present. In this competitive-binding type assay, the sample is incubated with a known titer of labeled amyloid protein and amyloid protein antibody. Antibody-protein complex is then separated from uncomplexed reagents using known techniques and the amount of label in the complexed material is measured, e.g. by gamma counting in the case of radioimmunoassay or photometrically in the case of enzyme immunoassay. The amount of amyloid protein in the sample, if any, is determined by comparing the measured amount of label with a standard curve.

Other embodiments of this basic principle include use of labeled antibodies per se, sandwich assays involving a three-way complex between analyte, anti-analyte antibody, and anti-antibody wherein one of the components contains a label, and separation of bound and unbound fractions using an immunoabsorbent. Agglutination assays which result in visible precipitates are also available (Limet et al., (1982) *J Clin Chem Clin Biochem* 20:142-147).

F. Screening Assay

The present assay provides one of the first steps in addressing the question whether preamyloid cortical deposits herald organic dementia. The concomitant appearance of preamyloid deposits and senile plaques suggests that preamyloid deposits may evolve into senile plaques.

Down's syndrome is the one known disease closely related to the proposed etiology of AD. As from their twenties onward, Down's patients develop the full spectrum of Alzheimer's changes, i.e., NFTs, congophilic angiopathy and senile plaques. As reported in Giacione et al., (1989) *Neurosci Letts* 97:232-238, a time-related analysis of preamyloid deposits and senile plaque distribution showed an age-dependent, inverse correlation between extracellular preamyloid deposits and senile plaque in Down's patients. While a similar, time-dependent study with Alzheimer's patients cannot be conducted, it is expected that a corresponding pattern (preamyloid turning to senile plaque deposits) would be found. therapeutic agents which interfere with this process promise the development of successful therapeutic regimens for Alzheimer's disease.

In the practice of the method of the invention, the expression of the amyloid protein is initiated by culturing the transformed cell line under conditions which are suitable for cell growth and expression of the amyloid protein. In this method, high level expression of the protein is preferred. In one embodiment of the invention, a CHO cell line transformed with a beta-actin vector comprising the DNA encoding the A42 or A99 amyloid protein is grown in a mammalian culture medium such as, for example, a 1:1 mixture of F12 medium and DME medium with 10% fetal calf serum for 5-72 hr at 37° C. Transfected viral monolayers are selected and plaque purified, and stocks of amyloid-vaccinia recombinant viruses are prepared.

The formation of the preamyloid aggregates can be monitored by standard immunocytochemical methods using, for example, beta-amyloid primary antibodies which are detected u sing a secondary, labeled anti-antibody. If one is interested in testing whether the compound of interest can inhibit preamyloid formation, the compound is introduced to the culture medium before monitoring for preamyloid aggregation. Alternatively, the compound is introduced to the culture medium after preamyloid formation has been established and this reaction mixture is monitored to see whether the compound induces amyloid resorption.

Potential therapeutic compounds for use in the present invention include, for example, amyloid-fibril denaturing agents such as dimethyl sulfoxide, and cytotoxic agents such as colchicine and chlorambucil. The efficacy of these agents may be monitored through observation of reduced antibody binding to the amyloid deposit. Reduction in such binding is indicative of reduced preamyloid deposition. Alternatively, preamyloid formation in the host cell may trigger other cellular events which cold be employed as markers unrelated to the etiology of Alzheimer's disease, but correlative with the presence of preamyloid deposits. For example, an increase in the level of certain enzymes, specifically proteases, may be measured in lieu of the preamyloid deposition. Typically, an increase in the concentration levels of these enzymes is observed when cultured cells are subjected to stress.

The present invention also encompasses kits suitable for the above diagnostic or screening methods. These kits contain the appropriate reagents and are constructed by packaging the appropriate materials, including the preamyloid protein aggregates immobilized on a solid support with labeled antibodies in suitable containers, along with any other reagents (e.g., wash solutions, enzyme substrate, anti-amyloid antibodies) or other materials required for the conduct of the assay. The reagents are usually premeasured for ease of use. An optional component of the kit is a set of instructions describing any of the available immunoassay methods. For example, a kit for a direct assay can comprise preamyloid protein aggregates immobilized on a solid immunoassay support and a container comprising labeled antibody to the amyloid protein, as well as the other reagents mentioned above.

The following examples are designed to elucidate the teachings of the present invention, and in no way limit the scope of the invention. Most of the techniques which are used to transform cells, construct vectors perform immunoassays, and the like are widely practiced in the art, and most practitioners are familiar with the standard resource materials which describe specific conditions and procedures. The examples are written in observation of such knowledge and incorporate by reference procedures considered conventional in the art.

EXAMPLE 1

Description of Amyloid Plaque Core DNA Constructs

The following examples describe the expression vectors containing the 42 amino acid plaque core region (A42), and the 42 amino acid plaque core region including the 57 amino acid adjacent carboxy-terminal region of the beta-amyloid precursor protein (A99). Alternative constructs for the A42 and A99 constructs were prepared which included a 17 amino acid amyloid signal sequence. As these constructs did not express the amyloid protein well, further experimentation with these vectors was not performed.

Recombinant vaccinia viruses bearing amyloid DNAs encoding each of the two amyloid constructs (VV:A42 and VV:A99) were generated by standard methods as reviewed by Mackett and Smith in (1986) *J Gen Virol* 67:2067-2082, which is incorporated herein by reference. FIG. 1 illustrates the various amyloid expression constructs, all of which were modified at the 5' end to satisfy the cloning constraints of the vaccinia P11 promoter in the pUV1 vector. Specifics for each construct are as follows:

A. VV:A42

The A42-encoding sequence (nucleotides 2080 to 2205, numbered in accordance with the 751 amyloid precursor sequence) was synthesized as a 145 basepair (bp) EcoRI-BamHI oligomer, provided below, containing the appropriate TGA stop codon and an amino-terminal Asn-Ser adaptor sequence:

5' AAT TCC GAT GCA GAA TTC CGA CAT GAC TCA
GGA TAT GAA GTT CAT CAT CAA AAA TTG GTG

```
                    -continued
TTC  TTT  GCA  GAA  GAT  GTG  GGT  TCA  AAC  AAA
GGT  GCA  ATC  ATT  GGA  CTC  ATC  GTG  GGC  GGT
GTT  GTC  ATA  GCG  TGA  TCT  AGA  TGA  G  3'
```

The synthetic fragment was ligated to EcoRI- and BamHI-digested pGem1 (Promegaa-Biotec), deriving pGemA42. The EcoRI-BamHI fragment of pGemA42 was subsequently isolated and ligated into the EcoRI-BamHI site of pUV1 deriving pUV1:A42.

The XbaI-SalI fragment of pUV1:A42 (287 bp) was further subcloned into mp18 for sequence confirmation.

B. VV:A99

The DNA encoding the amyloid protein for the pUV1-A99 constructs was derived from 4T4B, a plasmid encoding the 751 amino acid precursor protein. The construction of plasmid 4T4B is described in Example 3 of PCT/US87/02953, owned by the same assignee. The relevant portions of this publication are incorporated herein by reference. The 590 bp DdeI-PvuII fragment of plasmid 4T4B was isolated from the carboxy-terminal 1 kilobase (kb) EcoRI fragment of 4T4B and ligated with a 27 bp EcoRI-DdeI adaptor sequence and cloned into the EcoRI- and SmaI- digested pUV1, deriving pUV1:A99.

The 761 bp XbaI-SalI fragment of pUV1:A99 was further sublconed into the XbaI-SalI vector fragment of mp18 and pGem2. Sequence data confirmed the predicted sequence.

EXAMPLE 2

Expression of Amyloid Proteins

The vaccinia insertion vectors described in Example 1 were used to generate amyloid-vaccinia recombinant viruses as follows.

A. Preparation of Amyloid-Vaccinia Virus Recombinants

Confluent monolayers of CV-1 cells in 60 mm dishes were infected with vaccinia virus (Wyeth strain) at a multiplicity of infection (moi) of 0.05 pfu/cell. At 0.5 hr post-infection, the cells were transfected with a calcium phosphate precipitate of 10 ug insertion plasmid DNA and 0.5 ug wild-type vaccinia virus DNA. Cells were fed with complete medium and incubated at 37° C. for two days. Monolayers were collected and TK- vaccinia viruses were selected on TK-143 cells in the presence of 5-bromodeoxyuridine (BudR) at 25 ug/ml. At 48 hr after infection, monolayers were overlaid with 1% agarose containing 300 ug/ml 5-bromo-4-chloro-3-indolyl-B-D-galactopyranoside (Xgal). At 4-6 hr, blue plagues were picked and further purified by two additional rounds of plaque purification in the presence of BudR and Xgal. Stocks of the amyloid-vaccinia recombinant viruses were prepared in TK-142 or CV-1 cells. Recombinant viral DNA was prepared from each stock and was shown by Southern blot analysis to contain the appropriate amyloid DNA insert and to be free of contamination with wild-type or spontaneous TK- vaccinia.

B. Identification of Amyloid-specific Polypeptides Produced by Vaccinia Virus Recombinants Characterization of the CV-1 expressed VV:A42 and VV:A99 amyloid proteins was carried out employing immunoprecipitation and polyacrylamide gel analysis of $^{35}S$-methionine-labeled infected cell protein using antibodies directed against the carboxy-terminal region of the amyloid precursor.

The beta-amyloid antibodies were generated from synthetic peptides. The synthetic peptides were prepared using solid phase synthesis according to standard protocols. Purification of the crude peptides was accomplished by desalting with gel filtration followed by ion-exchange chromatography and preparative reverse-phase liquid chromatography. Each peptide was fully characterized by amino acid composition and sequence analysis. COOH-CORE corresponds to amino acids 653-680(DAEFRHDSGYEVHHQKLVFFAEDVG-SSA) (the carboxy-terminal two amino acids were taken from the amino acid sequence of Masters et al., (1985) Proc Natl Acad Sci 82:4245-4249 and are different in the deduced translation of the A4 cDNA of Ponte et al., supra. COOH-B2 and COOH-C2 correspond to amino acids 736-751 (NGYENPTYKFFEQMQN), COOH-B3 and COOH-C3 correspond to amino acids 705-719(KKKQYTSIHHGVVEV) and COOH-C5 corresponds to amino acids 729-742(HLSKMQQ-NGYENPT). Reference for the numbering of peptides along the topology of the A4 precursor is from Ponte et al., supra. New Zealand white rabbits were immunized intradermally with 500 ug of peptide conjugated to keyhole limpet hemocyanin. The rabbits were first bled at 4 weeks and 1 week later the rabbits were boosted with 250 ug conjugated peptide. Subsequent bleeds were done at 3 week intervals with boosts following 1 week later. All animals were treated in accordance with institutional guidelines. Antibody titers against the appropriate peptide were determined by enzyme-linked immunosorbent assays coupled with horseradish peroxidase and found to be $7.4 \times 10^4$, $2.7 \times 10^5$, $1 \times 10^5$, $9.1 \times 10^6$, $8.2 \times 10^5$, and $2.5 \times 10^5$ for COOH-CORE, COOH-B2, COOH-C2, COOH-B3, COOH-C3, and COOH-C5, respectively.

Antibodies to 9523 correspond to amino acids 673-685(AEDVGSKNGAIIG) and 9524 correspond to amino acids 701-712(LVMLKKQYTSI). Antibodies to these two peptides were generated by coinjecting New Zealand white rabbits each with 200 ug methylated bovine serum albumin (PBS) plus 200 ug of the respective synthetic peptide in PBS. Rabbits were boosted one, two and three weeks following primary inoculation with identical amounts of peptide. Serum samples were taken at week 6 and titered against APCP synthetic peptide. Titers achieved were $1.5 \times 10^4$ for 9523 and $4 \times 10^5$ for 9524.

CV-1 cells were infected with VV:99 at a multiplicity of invention of one. $^{35}S$-methionine (250 uCi/ml) was a deed at 20 hr post infection for 4 hr. Cell lysates were prepared and aliquots containing $10^7$ cpm were immunoprecipitated with amyloid-specific antisera (COOH-B3, COOH-C5 and COOH-CORE) or normal rabbit serum and protein A.

Figure 2:
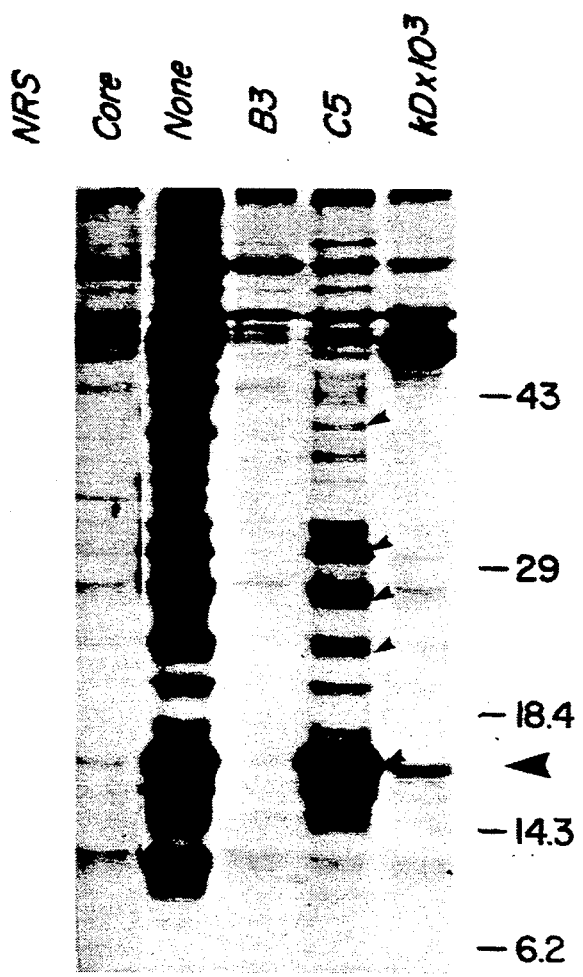
FIG. 2 illustrates the results of immunoprecipitation of $^{35}$S-methionine labeled VV:A99 infected CV-1 cell lysates using APCP antibodies. The arrows mark A99 protein.
Figure 3A:
FIGS. 3A-D are fluorescent photomicrographs of infected CV-1 cells stained with APCP antibodies.
Figure 3B:
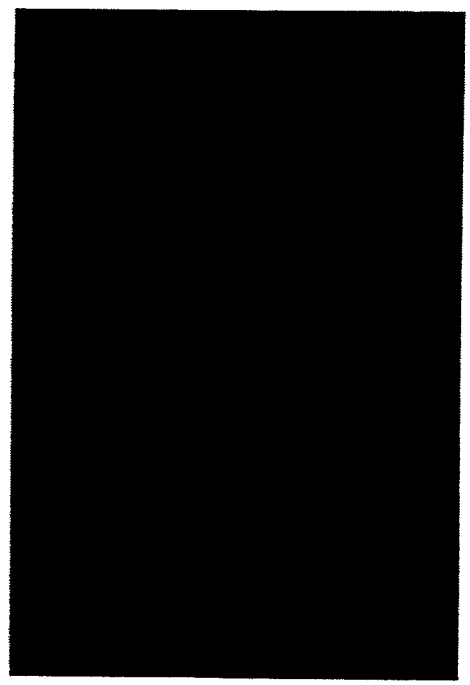
Figure 3C:
Figure 3D:

Immunoprecipitates of $^{35}S$-methionine cell lysates were anlaysed on denaturing 20% SDS-polyacrylamide gels. As shown in FIG. 2, high levels of expression and stability of the A99 protein generated by VV:A99 was demonstrated. The control sera (normal, nonimmune rabbit sera) did not display reactivity with the VV:A99 protein product. The VV:A99 amyloid core protein migrated as a broad band spanning approximately 11.5-17 kd molecular weight. In addition, higher molecular weight forms of the A99 protein were clearly observed.

The expression product of VV:A99 demonstrated high level expression of the 99 amino acid core protein and showed evidence of self-aggregation as well as aggregation with other proteins or self-aggregation combined with proteolysis since multimers of A99 did not always occur in integers of 11.5-17 kd.

EXAMPLE 3

Staining of A42 and A99 Expressing Cells

Two human, SK-N-MC (ATCC #HTB10) and IMR-32, (ATCC #CCL127) and one rat, PC-12 (Green and Tischler, (1976) *Proc Natl Acad Sci USA* 73:2424-2428) neuoronal cell lines were examined for their ability to permit efficient infection with the VV:A42 and VV:A99 recombinant viruses. All cell lines were documented as permissive hosts for vaccinia virus replication by infecting cells with a given amount (moi=2) of vaccinia virus of known titer. The infected cells were harvested 20 hours after infection, disrupted by freeze-thaw, and then titered. The yield was compared to the input viral units and if 20-100 fold increase results, the host cell was considered permissible for vaccinia replication.

These neuronal lines and the CV-1 cell line were employed for amyloid staining studies. The culture medium for each host was as follows:

| | |
|---|---|
| CV-1: | The medium Eagle MEM supplemented with 10% FBS, penicillin, streptomycin and L—Gln. |
| SK-N-MC: | Eagle MEM supplented with 10% FBS, non-essential amino acids, penicillin, streptomycin and L—Gln. |
| PC-12: | DMEM21, 5% DHS, 5% DFBS and L—Gln; and |
| IMR-32: | Eagle MEM (Hank's BSS) and 10% deltaFBS plus nonessential amino acids, penicillin, streptomycin and L—Gln. |

Each cell line was grown to confluency on a microscope slide divided into 4 individual chambers (Lab Tech). One chamber was mock infected, the second infected with a control recombinant virus lacking A4 sequences (VV:CONT), the third chamber infected with VV:A99, and the fourth chamber infected with VV:A42. This is an internally controlled method since each slide was manipulated as a single unit.

Viral infections were carried out at a moi from 5 to 20 viral plaque forming units (pfu) per cell and were harvested for staining at approximately 20 hours post infection. Slides prepared for immunocytochemistry were fixed with 4% paraformaldehyde and permeabilized with 0.2% Trtion X-100 prior to treatment with primary and rhodamine-conjugated second antibodies (Capell Labs). Briefly, after permeabilization, cells were washed with PBS containing 0.2% gelatin. 100 ul of primary amyloid antibody (diluted 1/200 with PBS plus 0.2% gelatin) was incubated on the cells at 37° C. for 30 minutes. Cells were washed for 10 minutes in PBS and 0.2% gelatin, then incubated at 37° C. for 20 minutes with a 1/200 dilution (in PBS and gelatin) of secondary antibody (goat-anti-rabbit) tagged with Rhodamine. Cells were washed for 10 min in PBS and gelatin, then mounted for visualization in a fluorescent microscope. Antibodies used with success included 9523, 9524, B3 and C5. CORE antibodies were not assessed. Alternatively, the slides were fixed in 4% paraformaldehyde then stained with Thioflavin S or Congo red, and conuterstained with hematoxylin according to directions in commercial kits (Sigma).

IMR-32 and PC-12 cells presented some technical difficulties and thus further investigation with these cell lines was terminated. The IMR-32 cells did not adhere well to the microscope slides, which could be alleviated by pretreatment with laminin, and, moreover, the IMR-32 cells did not tolerate the serum-free conditions during the infections. PC-12 cells showed high background immunostaining, hence, differences between experimental and control samples were not dramatic.

FIG. 3 shows fulorescent photomicrographs of CV-1 cells stained with 1/200 dilutions of the core domain antibodies 9523 antibodies. Specific and robust staining was seen in only the VV:A99 and VV:42 infected cells. VV:99 specific staining, but not VV:42 staining, was seen with the B3 antibody as would be anticipated since this region is not included in the VV:A42 construct (results not shown). Faint punctuate staining was observed for both antibodies on all cells presumably due to endogenous A4 precursor expression. The VV:A99 and VV:A42 infected cells displayed strong reactivity in the form of large deposit-like structures which are cell associated. The deposit-like structures are probably not cell debris from the viral cytopathicity since they are not seen in the VV:CONT cells and their immunoreactivity could be eliminated by preadsorption of the antisera with the synthetic peptide used to raise the serum.

The possible potentiating effect of aluminum on deposit formation was investigated by pretreating the cells with 50 mM $AlCl_3$. Aluminum might be considered a "cofactor" in the pathology of amyloid formation since it is present in plaques. However, no obvious qualitative difference in the degree of deposit formation between cultures treated and untreated with aluminum was found.

It seems relevant that several researchers investigating A4 core domain immunoreactivity in brains of Alzheimer's victims describe similar structures as those in FIG. 3. Each group reported finding significant amounts of specifically stained spherical, granular deposits which were considerably smaller than pre-plaques and plaques (Davies et al., (1988) *Neurolog* 38:1688-1693; Ikeda et al., (1989) *Lab Invest* 60:113-122; Tagliavini et al., (1988) supra; Tate-Ostroff et al., (1989) *Proc Natl Acad Sci* 86:745-749). All research groups independently propose that the observed small granular deposits are the very early stages of amyloid plaque development. The structures observed in our cell culture system are analogous to those seen in the Alzheimer's diseased brain. It was noted by these investigators that the granular deposits could be occasionally detected with silver stain but not with Congo red. Because the Alzheimer's granular deposits were highly reactive with A4 antisera but were not easily reacted with stains capable of recognizing the tinctorial properties of amyloid, the structures were termed "preamyloid" deposits.

EXAMPLE 4

Establishment of Stable Cell Lines

Figure 4:
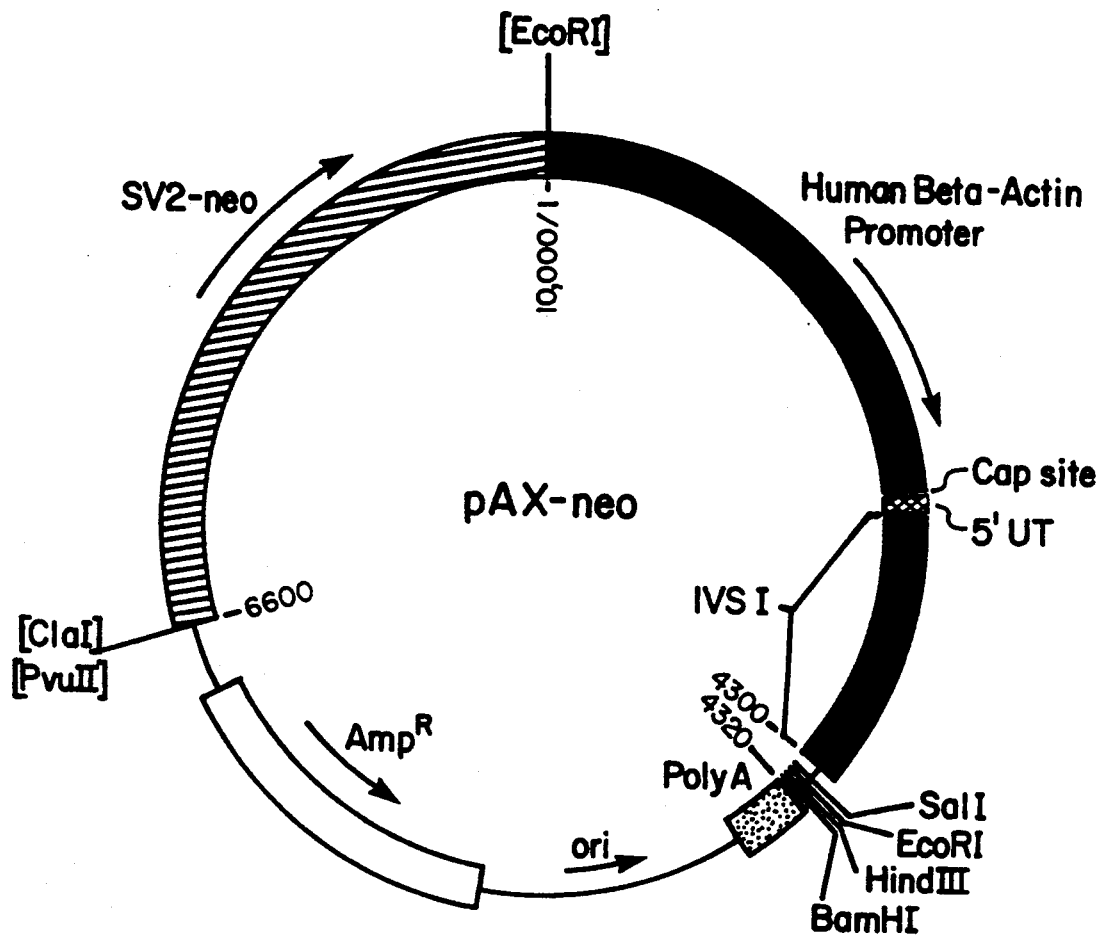
FIG. 4 is a illustration of the modified beta-actin expression selection vector, pAX-neo, that was employed to express the beta-amyloid core constructs in mammalian cells.

A number of constructs expressing the beta-amyloid core protein were constructed using a derivative of the beta-actin expression/selection vector designated pHbetaAPr-1-neo. This vector, illustrated in FIG. 4, is a combination of the following elements:

a) bp 1-4300 is the 4.3 kb EcoRI-AluI fragment from the human beta-actin gene isolate p14Tbeta-17 (Leavitt et al., (1984) *Mol Cell Biol* 4:1961-1969). For sequencing details of the promoter see Ng et al., (1985) *Mol Cell*

Biol 5:2720≧2732. The cap site, 5' untranslated region and IVS 1 positions are indicated in FIG. 4. There is no ATG codon present in the 5' UT nor in the polylinker region from the 3' splice site to the BamHI site;

b) bp 4300-4320 is in part derived from pSP64 polylinker (Melton et al., (1984) *Nuc Acids Res* 12:7035-7056);

c) bp 4320-6600 is derived from pcDV1 (Okayama & Berg, (1983) *Mol Cell Biol* 3:280-289); and d) bp 6600-10000 is the PvuII-EcoRI fragment from pSV-neo (Southern & Berg (1982) *J Mol App Genet* 1:327-341) containing the bacterial neomycin gene linked to the SV40 origin plus early promoter. The direction of transcription is as indicated in FIG. 4. This vector was altered by deleting the EcoRI site and adding a new EcoRI site within the polylinker 3' to the SalI site and 5' to the HindIII site. This modified vector is designated pAX-neo. Beta-actin A42 was constructed by excising the EcoRI-BamHI 145 bp fragment from pGEM-A42, adding a SalI-EcoRI adaptor sequence (5'-TCG ACA TGG ATG CAC AAT TA-3') and cloning into the pAX-neo expression vector at the SalI and BamHI sites. The beta-actin A99 plasmid was constructed by excising the 670 bp EcoRI-HindIII fragment of pGEM$_2$-A99, adding the above-described SalI-EcoRI adaptor sequence and cloning into the pAX-neo vector at the SalI and HindIII sites.

Each construct was introduced into CHO cells by the calcium phosphate precipitation method using 7 ug of each DNA per $10^6$ cells, and a resistant population was selected with G418-neomycin. The efficiency of transfection for the A99 or A42 constructs was over $10^3$ for $10^6$ cells and pools of cells transfected with either beta-actin A99 or with beta-actin A42 were selected using G418-neomycin resistance (500 ug/ml).

Cell lysates from these pools are prepared and analyzed by immunoprecipitation of the A4 proteins as well as by Western blotting. High expressing clones are then selected and assayed for "preamyloid" deposits using the immunocyto-staining procedures described in Example 3.

EXAMPLE 5

Assay for Preamyloid Deposition

Cells infected with VV:99 or VV:42 which are capable of forming amyloid deposits are plated in a 96-well microtiter plate. To make the appropriate dilutions and additions, an automated pipetter is used to introduce the drug to be tested to the cells. A range of concentrations of the drug is incubated in a tissue culture incubator (or preincubated) with the cells at 37° C. for a predetermined time period, or alternatively, for 3 to 72 hours.

Following incubation, the culture media is removed, and the cells are prepared for preamyloid measurement as follows. The cells are fixed for immunocytochemical staining with amyloid antibodies. The primary antibodies are introduced followed by incubation with labelled, secondary anti-antibodies and the level of binding between the primary and secondary antibodies is measured using an ELISA plate reader to record the optical density of the labeled antibody. A smaller optical density reading as compared to a control sample of cells grown in the absence of the test drug is indicative of that drug's ability to inhibit amyloid deposition. This procedure may be modified to permit detection of preamyloid dissolution using a correlative enzyme marker.

It will be apparent to those skilled in the art that various modifications and variations can be made in the method of the present invention without departing from the scope or spirit of the invention. Thus, it is intended that the claims cover the modifications and variations of the invention.

What is claimed is:

1. A method of screening agents capable of affecting the amount of preamyloid deposits, comprising:
    a) culturing a cell line transfected with a DNA sequence which encodes and intracellularly expresses the following polypeptide:

0
Met
                                    10
Asp Ala Glu Phe Arg His Asp Ser Gly Tyr Glu Val His Gln
         20                                    30
Lys Leu Val Phe Phe Ala Glu Asp Val Gly Ser Asn Lys Gly Ala
                          40    (42)
Ile Ile Gly Leu Met Val Gly Gly Val Val Ile Ala Thr Val Ile
              50                                    60
Val Ile Thr Leu Val Met Leu Lys Lys Lys Gln Tyr Thr Ser Ile
                         70
His His Gly Val Val Glu Val Asp Ala Ala Val Thr Pro Glu Glu
                   80                                    90
Arg His Leu Ser Lys Met Gln Gln Asn Gly Tyr Glu Asn Pro Thr
                                (99)
Tyr Lys Phe Phe Glu Gln Met Gln Asn or the first 42 amino acids thereof the DNA sequence expressing a β-amyloid protein as an insoluble, preamyloid aggregate inside the cell which preamyloid aggregate is not detected with Congo red stain;
    b) combining a known quantity of the agent to be tested with the cell culture; and
    c) monitoring the combination to determine the effect on the amount of preamyloid aggregate.

2. The method of claim 1 wherein the DNA sequence encodes the first 42 amino acids of said polypeptide.

3. The method of claim 1 wherein the DNA sequence encodes all 99 amino acids of said polypeptide.

4. The method of claim 1 wherein the cell lines are transfected with the DNA sequence using recombinant vaccinia virus.

5. The method of claim 1 wherein the cell lines are derived from mammalian host cells.

6. The method of claim 1 wherein the agent to be tested is introduced during the growth phase of the cell culture to determine whether the agent inhibits preamyloid aggregate formation.

7. The method of claim 1 wherein the agent to be tested is added to the preamyloid aggregate to determine whether the agent dissolves the preamyloid aggregate.

* * * * *